United States Patent
Tanizaki

(10) Patent No.: US 9,119,449 B2
(45) Date of Patent: Sep. 1, 2015

(54) BIOLOGICAL INFORMATION MEASUREMENT DEVICE AND PROTECTIVE COVER

(71) Applicant: Panasonic Healthcare Holdings Co., Ltd., Minato-ku, Tokyo (JP)

(72) Inventor: Yoichi Tanizaki, Ehime (JP)

(73) Assignee: Panasonic Healthcare Holdings Co., Ltd., Minato-ku, Tokyo (JP)

( * ) Notice: Subject to any disclaimer, the term of this patent is extended or adjusted under 35 U.S.C. 154(b) by 0 days.

(21) Appl. No.: 14/413,710

(22) PCT Filed: Jun. 28, 2013

(86) PCT No.: PCT/JP2013/004034
§ 371 (c)(1),
(2) Date: Jan. 9, 2015

(87) PCT Pub. No.: WO2014/013681
PCT Pub. Date: Jan. 23, 2014

(65) Prior Publication Data
US 2015/0136818 A1   May 21, 2015

(30) Foreign Application Priority Data

Jul. 20, 2012 (JP) .................................. 2012-161183
Apr. 9, 2013 (JP) .................................. 2013-080948

(51) Int. Cl.
*A45C 11/00* (2006.01)
*A61B 5/1473* (2006.01)
(Continued)

(52) U.S. Cl.
CPC ............... *A45C 11/00* (2013.01); *A61B 5/1473* (2013.01); *G01N 33/48785* (2013.01); *G01N 33/66* (2013.01); *A61B 5/14532* (2013.01); *A61B 2562/24* (2013.01)

(58) Field of Classification Search
CPC ....................................................... A45C 11/00
USPC ................ 206/305, 306, 320, 37, 3, 7.1, 569; 422/68.1, 63
See application file for complete search history.

(56) References Cited

U.S. PATENT DOCUMENTS 3,756,384 A * 9/1973 Stone ............................ 206/534
4,122,947 A * 10/1978 Falla ............................ 206/569
(Continued)

FOREIGN PATENT DOCUMENTS

GB          2333402 A      7/1999
JP       2003-107092 A     4/2003
(Continued)

OTHER PUBLICATIONS

The Search Report from the corresponding International Patent Application No. PCT/JP2013/004034 issued on Aug. 6, 2013.

*Primary Examiner* — Steven A. Reynolds
*Assistant Examiner* — King M Chu
(74) *Attorney, Agent, or Firm* — Shinjyu Global IP

(57) ABSTRACT

The cover body is an elastic member integrally formed of the upper side, the lower side, and the lateral side. The upper side preferably includes a display viewable window at a first end, and the lateral side preferably includes a sensor insertion opening at a second end opposite the first end with the display being viewable window on the upper side. The sensor insertion opening preferably includes a tubular protuberance configured to cover an outer circumference of the sensor insertion opening and protrudes outwardly from the sensor insertion opening.

13 Claims, 3 Drawing Sheets

(51) Int. Cl.
*G01N 33/66* (2006.01)
*G01N 33/487* (2006.01)
*A61B 5/145* (2006.01)

(56) References Cited

U.S. PATENT DOCUMENTS

| | | | | |
|---|---|---|---|---|
| 4,824,059 | A * | 4/1989 | Butler | 248/176.1 |
| 5,142,384 | A * | 8/1992 | Wood et al. | 359/3 |
| 5,186,900 | A * | 2/1993 | Jensen et al. | 422/550 |
| 5,360,108 | A * | 11/1994 | Alagia | 206/320 |
| 5,388,691 | A * | 2/1995 | White | 206/305 |
| 5,388,692 | A * | 2/1995 | Withrow et al. | 206/320 |
| 5,850,754 | A * | 12/1998 | Dobbins | 70/456 R |
| 6,296,164 | B1 * | 10/2001 | Russo | 224/602 |
| 6,490,893 | B1 * | 12/2002 | Benion | 70/63 |
| 6,948,614 | B1 * | 9/2005 | Hall et al. | 206/305 |
| 7,370,763 | B1 * | 5/2008 | Pascucci | 206/569 |
| 7,417,193 | B2 * | 8/2008 | Schumacher et al. | 174/135 |
| 8,087,271 | B1 * | 1/2012 | Patton | 70/63 |
| 8,394,343 | B2 * | 3/2013 | Chan et al. | 422/555 |
| 8,453,835 | B2 * | 6/2013 | So | 206/320 |
| 8,509,865 | B1 * | 8/2013 | LaColla et al. | 455/575.8 |
| 8,711,568 | B2 * | 4/2014 | Evens | 361/728 |
| 2001/0002003 | A1 * | 5/2001 | Kuzdak et al. | 206/38.1 |
| 2003/0021729 | A1 * | 1/2003 | Moller et al. | 422/68.1 |
| 2003/0038047 | A1 * | 2/2003 | Sleva et al. | 206/370 |
| 2003/0223906 | A1 * | 12/2003 | McAllister et al. | 422/58 |
| 2004/0173488 | A1 * | 9/2004 | Griffin et al. | 206/363 |
| 2005/0074368 | A1 | 4/2005 | Moller et al. | |
| 2005/0087467 | A1 * | 4/2005 | Dao | 206/459.1 |
| 2005/0087468 | A1 * | 4/2005 | Siethoff et al. | 206/459.1 |
| 2005/0167300 | A1 * | 8/2005 | Hamaguchi | 206/305 |
| 2005/0205435 | A1 * | 9/2005 | Loy | 206/37 |
| 2006/0040333 | A1 * | 2/2006 | Zocchi | 435/14 |
| 2007/0056871 | A1 * | 3/2007 | Griffiths et al. | 206/459.1 |
| 2007/0080093 | A1 * | 4/2007 | Boozer et al. | 206/569 |
| 2007/0144922 | A1 * | 6/2007 | Imoarai et al. | 206/204 |
| 2007/0261978 | A1 * | 11/2007 | Sanderson | 206/320 |
| 2008/0053851 | A1 * | 3/2008 | Ko et al. | 206/320 |
| 2008/0053852 | A1 * | 3/2008 | Ko et al. | 206/320 |
| 2009/0009945 | A1 * | 1/2009 | Johnson et al. | 361/681 |
| 2009/0032421 | A1 * | 2/2009 | Sween et al. | 206/320 |
| 2009/0057188 | A1 * | 3/2009 | Kroll et al. | 206/569 |
| 2009/0152159 | A1 * | 6/2009 | Beeman | 206/570 |
| 2010/0044261 | A1 * | 2/2010 | Yao et al. | 206/370 |
| 2010/0078343 | A1 * | 4/2010 | Hoellwarth et al. | 206/320 |
| 2011/0073505 | A1 * | 3/2011 | Stiehl | 206/320 |
| 2012/0211500 | A1 * | 8/2012 | Amron | 220/592.16 |
| 2012/0267277 | A1 * | 10/2012 | Frederick et al. | 206/459.1 |
| 2014/0299506 | A1 * | 10/2014 | Engimann, III | 206/569 |

FOREIGN PATENT DOCUMENTS

| | | |
|---|---|---|
| JP | 2004-313269 A | 11/2004 |
| JP | 2007-248209 A | 9/2007 |
| JP | 4362269 B2 | 11/2009 |
| JP | 4676363 B2 | 4/2011 |
| JP | 2013-050326 A | 3/2013 |

\* cited by examiner

BIOLOGICAL INFORMATION MEASUREMENT DEVICE AND PROTECTIVE COVER

This application is a U.S. National stage application of International Application PCT/JP2013/04034, with an international filing date of Jun. 28, 2013, which claims priority to Japanese Patent Application No. 2013-080948 filed on Apr. 9, 2013 and Japanese Patent Application No. 2012-161183 filed on Jul. 20, 2012. The entire disclosures of International Application PCT/JP2013/04034, Japanese Patent Application No. 2013-080948 and Japanese Patent Application No. 2012-161183 are hereby incorporated herein by reference.

TECHNICAL FIELD

Embodiments of the prevent invention relate to a protective cover used for a biological information measurement device that measures biological information including the blood glucose level from blood. It also relates to a biological information measurement device with the protective cover on.

BACKGROUND

A biological information measurement device includes a body case having a display part and an operation part on its upper side, and a sensor mounting part on its lateral side. The body case is divided into an upper part and a lower part. Various components are housed in the body case, and then, the upper and lower parts are unified.

There is a known body case having a cover on its upper side and partly on its lateral side so that the cover can protect the body case from damage due to falling.

Biological information measurement devices have been required to reduce the risk of infection. However, known biological information measurement devices with covers such as the one discussed above are not capable of reducing infection risk.

Particularly, the body case, divided into upper and lower parts, does not have a cover on the joints of the divided body case, and the joints between the upper and lower parts of the body case tend to receive blood. It is difficult for a user to cleanse blood adhered to the joints with a washcloth or the like. Therefore, there is an infection risk caused by blood adhered to the joints between the upper and lower parts.

SUMMARY OF INVENTION

A protective cover for a biological information measurement device according to the present invention, comprising: an upper side; a lower side opposing the upper side with a predetermined interval therebetween; and a lateral side extending along a side circumference of the protective cover between the upper side and lower side. The upper side, the lower side, and the lateral side are preferably integrally formed of an elastic member, the upper side preferably includes at one end thereof a display viewable window, and the lateral side preferably includes a sensor insertion opening at the other end opposing the one end with the display viewable window on the upper side. The sensor insertion opening includes a tubular protuberance configured to cover an outer circumference of the sensor insertion opening. The tubular protuberance protrudes outwardly from the sensor insertion opening.

DETAILED DESCRIPTION

Embodiments of the present invention will be described with reference to the drawings.

The present invention should not be limited to the embodiments as described below.

Figure 1:
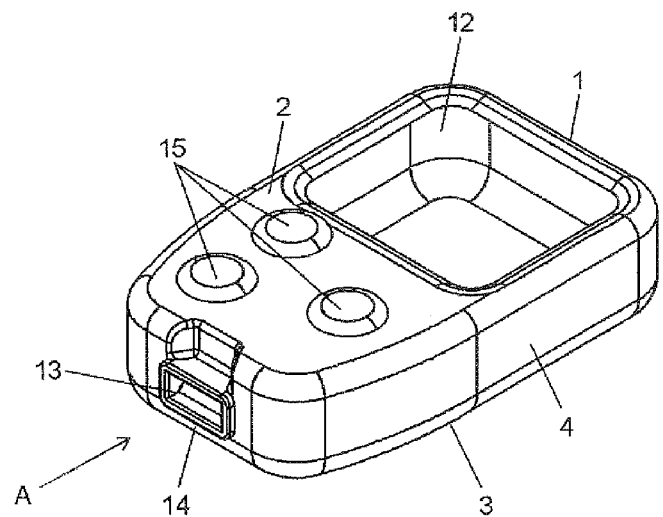
FIG. 1 is a perspective view of a protective cover for a biological information measurement device, according to an embodiment of the present invention.

FIG. 1 shows a protective cover for a biological information measurement device according to an embodiment of the present invention. The cover body 1 having a substantially cuboid shape includes an upper side 2, a lower side 3 opposing the upper side 2 with a predetermined interval therebetween and a lateral side 4 covering a side circumference of the cover body between the upper side 2 and the lower side 3. In use, a biological information measurement device 5 (typically by a blood glucose level measurement device as shown in FIG. 2) is inserted in the cover body 1 forming the protective cover for a biological information measurement device.

Figure 2:
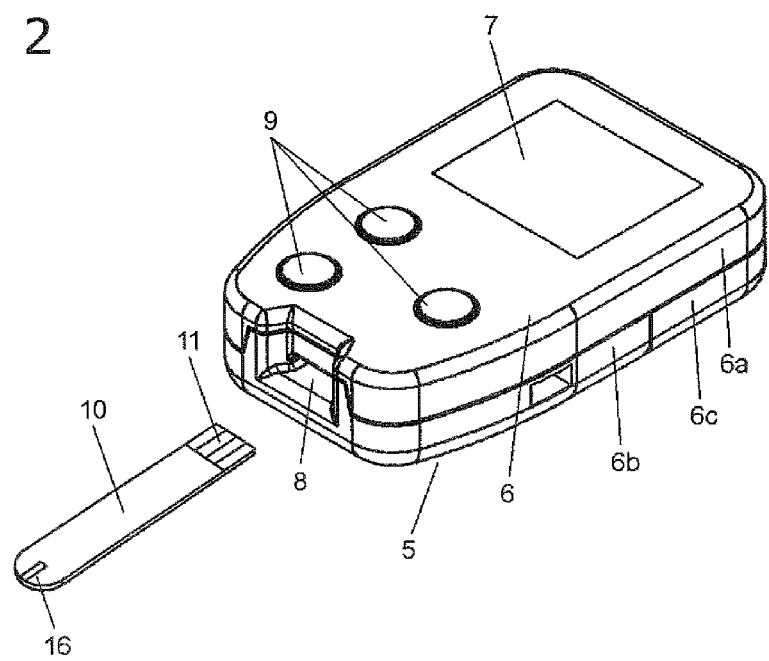
FIG. 2 is a perspective view of the biological information measurement device with the protective cover on, according to an embodiment of the present invention.

As shown in FIG. 2, the biological information measurement device 5 includes a body case 6 having a substantially cuboid shape. The body case 6 includes a display part 7 at one end of its upper side and a sensor mounting part 8 at the other end of its lateral side opposing the one end with the display part 7. Furthermore, the upper side of the body case 6 between the display part 7 and the sensor mounting part 8 is provided with a plurality of operating buttons 9 that bulge from the upper side of the body case 6. For measurement of a blood glucose level, connecting terminals 11 of a rectangular plate-like blood glucose level sensor 10 are connected to the sensor mounting part 8.

The cover body 1 will now be discussed in detail with reference to FIG. 1 again.

The cover body 1 includes at one end of the upper side 2 a display viewable window 12 corresponding to the display part 7 of the biological information measurement device 5. The display part viewable window 12 is as large as the display part 7 of the biological information measurement device 5. Even when the biological information measurement device 5 is inserted in the cover body 1, the display part 7 of the biological information measurement device 5 is still viewable.

As is apparent from FIG. 1, the display viewable window 12 extends close to one end of the upper side 2. Furthermore, the display viewable window 12 extends close to two lateral sides of the upper side 2 but not to the other end of the upper side 2. The lower side 3 of the cover body 1 covers an entire lower side of the biological information measurement device 5 shown in FIG. 2.

The cover body 1 has a pouch-like shape with an opening of the display viewable window 12, integrally formed by the upper side 2, lower side 3 and lateral side 4 using silicon rubber as an example of an elastic member.

The cover body 1 has a sensor insertion opening 13 substantially in the center of the lateral side 4 at its one end opposing the display viewable window 12 on the upper side 2, in such a manner that the sensor insertion opening 13 faces the sensor mounting part 8 of the biological information measurement device 5. The sensor insertion opening 13 is formed slightly larger than the sensor mounting part 8 of the biological information measurement device 5, and therefore, it does not interfere when a blood glucose level sensor 10 is mounted on the sensor mounting part 8.

According to this embodiment, the sensor insertion opening 13 includes a rectangular tubular protuberance 14 covering an outer circumference of the sensor insertion opening 13 and protruding outwardly from the sensor insertion opening 13. The protuberance 14 protrudes in a direction opposite the illustrated insertion direction A in which a blood glucose level sensor 10 is inserted into the sensor insertion opening 13.

As shown in FIG. 2, the biological information measurement device 5 has a reduced width from its middle portion to the end where the sensor mounting part 8 is. In other words, the biological information measurement device 5 is formed slightly narrower on its sensor mounting part 8 side and is therefore easy for a user to hold in one hand. Furthermore, as shown in FIG. 1, the cover body 1 has a reduced width from its middle portion to the end where the sensor insertion opening 13 is, having a similar outer shape as the biological information measurement device 5.

The cover body 1 includes operating portions 15 corresponding to the plurality of operating buttons 9 of the biological information measurement device 5 and bulging from the upper side 2 between the display viewable window 12 and the sensor insertion opening 13. The upper side 2 with the operating portions 15 is formed thinner than the lower side 3 and the lateral side 4, so that a user can press the operating buttons 9 of the biological information measurement device 5 through the upper side 2 of the cover body 1.

The cover body 1 is formed such that the upper side 2, lower side 3, and lateral side 4 adhere tightly to the upper, lower, and circumferential lateral side of the biological information measurement device 5 when the biological information measurement device 5 is inserted into the cover body 1 through the display viewable window 12.

The following is a description of how the protective cover for a biological information measurement device with the above configuration.

First, the sensor mounting part 8 side of the biological information measurement device 5 is inserted in the pouch-like shaped cover body 1 through the display viewable window 12 provided on one end of the upper side 2. Since the biological information measurement device 5 is formed narrower between its middle portion and the sensor mounting part 8 side as discussed above, it can be easily inserted through the widely opened display viewable window 12.

In this state, the biological information measurement device 5 is further inserted into the cover body 1 toward the sensor insertion opening 13 on the other end. The cover body 1 is elastic as discussed above. Using its elasticity, the biological information measurement device 5 stretches out the display viewable window 12 while being inserted into the cover body 1. After the insertion of the biological information measurement device 5, the cover body 1 restores its original shape by its elasticity and adheres tightly to an outer face of the biological information measurement device 5.

When the biological information measurement device 5 is inserted into the cover body 1, the air in the cover body 1 is compressed in accordance with the insertion of the biological information measurement device 5. Since the cover body 1 has the sensor insertion opening 13 in the lateral side 4 on the other end of the upper side 2, the air can be released from the opening, and therefore, the biological information measurement device 5 can be easily inserted into the cover body 1.

The biological information measurement device 5 is further inserted into the cover body 1 until the sensor mounting part 8 of the biological information measurement device 5 aligns with the sensor insertion opening 13 of the cover body 1. Then, the entire body of the biological information measurement device 5 is pushed into the cover body 1, thereby completing the insertion. Then, the pouch-shaped cover body 1 covers the biological information measurement device 5 with the sensor insertion opening 13 facing the sensor mounting part 8 in such a manner that: (1) the upper side 2 covers the upper side of the biological information measurement device 5 excluding an area of the display part 7, (2) the lower side 3 covers the entire lower side of the biological information measurement device 5, and (3) the lateral side 4 covers the entire lateral side of the biological information measurement device 5.

The user then starts measuring blood glucose level.

First, the user mounts a blood glucose level sensor 10, as shown in FIG. 2, on the sensor mounting part 8 of the biological information measurement device 5. The blood glucose level sensor 10 is mounted through the sensor insertion opening 13 of the cover body 1. Then, the user makes a puncture in their index finger, for example, to draw their blood. After the drawn blood is deposited on a deposit portion 16 of the blood glucose level sensor 10, the biological information measurement device 5 measures a glucose level in the blood and displays the measured value on the display part 7. The user presses the operating buttons 9 of the biological information measurement device 5 through the operating portions 15 of the cover body 1.

At the time of the measurement and operation of the biological information measurement device 5, part of the blood deposited on the deposit portion 16 of the blood glucose level sensor 10 or part of the blood drawn from a user's finger by puncture may accidentally spatter and adhere to the biological information measurement device 5 in the part where blood is difficult to remove.

The body case 6 of the biological information measurement device 5 is composed of an upper case 6a and a lower case 6b that are separated as shown in FIG. 2. The lower case 6b further includes a separate battery cover 6c. Once blood adheres to a joint between the separate cases, it is difficult for a user to cleanse the adhered blood with a washcloth, or remove the blood completely. As a result, there occurs an infection risk caused by the blood adhering to such a joint.

When the biological information measurement device 5 is inserted into the protective cover for a biological information measurement device according to this embodiment, the upper, lower and outer lateral sides of the biological information measurement device 5 are sealed, respectively, by the upper side 2, lower side 3, and lateral side 4 of the cover body 1. Therefore, all joints in the biological information measurement device 5 are covered by the cover body 1 so as not to be exposed to the outside. As a result, blood is prevented from going in through the joints in the biological information measurement device 5, thereby reducing the risk of infection caused by blood adhered to the biological information measurement device 5.

Since the display part 7 of the biological information measurement device 5 is formed flat, the user can easily remove blood adhered to the display part 7. Furthermore, since the cover body 1 seals the biological information measurement device 5, spattered blood will not reach the joints through the display viewable window 12.

As a result, the risk of infection caused by blood adhered to the biological information measurement device 5 can be significantly reduced.

According to this embodiment, the sensor insertion opening 13 of the cover body 1 has a rectangular tubular protuberance 14 covering an outer circumference of the sensor insertion opening 13. The rectangular tubular protuberance 14 preferably protrudes outwardly from the sensor insertion opening 13. In this way, the risk of infection can be further reduced.

The protuberance 14 is preferably provided on the outer circumference of the sensor insertion opening 13 of the cover body 1, and the protuberance 14 protrudes in a direction opposite the illustrated insertion direction A in which a blood glucose level sensor 10 is inserted into the sensor insertion opening 13, as discussed above. Therefore, the sensor insertion opening 13 is located inside the protuberance 14 and can be seen only from the insertion direction A.

Accordingly, the user can insert a blood glucose level sensor 10 into the sensor mounting part 8 of the biological information measurement device 5 via the sensor insertion opening 13, in the insertion direction A.

Furthermore, the rectangular tubular protuberance 14 protrudes outwardly from the sensor insertion opening 13. Therefore, even when the user puts, for example, his index finger close to the sensor insertion opening 13 from a direction other than the insertion direction A, the finger only touches the protuberance 14 on the cover body 1, and therefore, the sensor mounting part 8 of the biological information measurement device 5 is prevented from being touched. Accordingly, the user's finger is prevented from touching the sensor mounting part 8 of the biological information measurement device 5 that is difficult to clean.

Even when the user accidentally puts his finger close to the sensor insertion opening 13 from the insertion direction A, since the rectangular tubular protuberance 14 protrudes in a direction opposite to the insertion direction A and is vertically narrow, the finger is prevented from being inserted into the protuberance 14. Accordingly, the sensor mounting part 8 of the biological information measurement device 5, which is difficult for the user to clean, is prevented from being touched by the user's finger.

As a result, the risk of infection can be further reduced.

The opening of the sensor mounting part 8 of the biological information measurement device 5 is preferably formed small as to prevent blood or dust from going into the biological information measurement device 5. This makes it difficult for the user to see where the blood glucose level sensor 10 is to be inserted.

Figure 3:
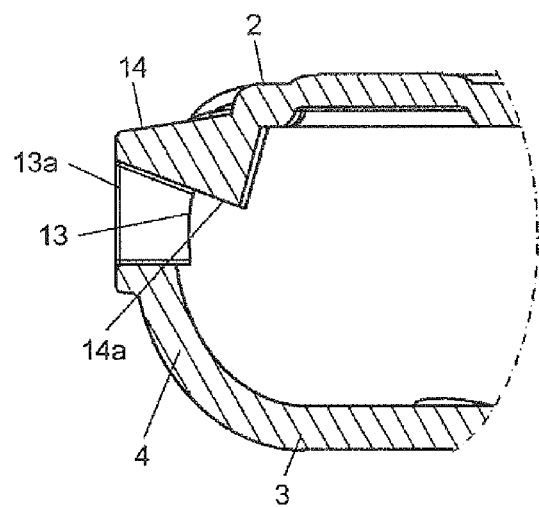
FIG. 3 is a cross sectional view of a main part of the protective cover for a biological information measurement device, according to an embodiment of the present invention.

The protuberance 14 in this embodiment has a front end opening 13a that is larger than the sensor insertion opening 13 at the back, as shown in FIG. 3. Particularly, the front end opening 13a, the sensor insertion opening 13, and the sensor mounting part 8 of the biological information measurement device 5 are increasingly large.

Accordingly, the user can see the protuberance 14 protruding from the cover body 1 to recognize where the blood glucose level sensor 10 is to be inserted. They can see the wide front end opening 13a at the front end of the protuberance 14 to determine in what part the blood glucose level sensor 10 is to be inserted. Therefore, it is easier for the user to use the device while the risk of infection can be reduced.

Figure 4:
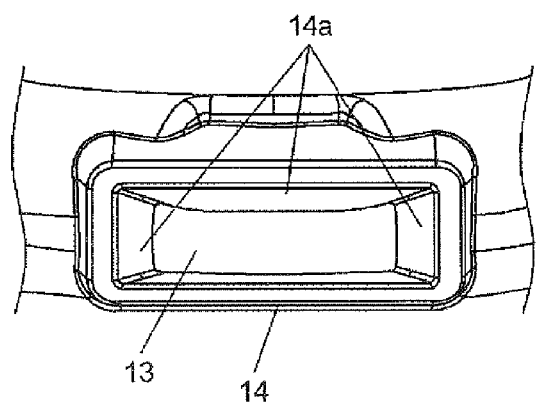
FIG. 4 is a front view of a main part of the protective cover for a biological information measurement device, according to an embodiment of the present invention.

As shown in FIG. 3 and FIG. 4, the inside of the protuberance 14 has an upper inner face and two inner lateral side faces forming guide faces 14a sloping from the front end opening 13a to the sensor insertion opening 13 at the back. With this configuration, a blood glucose level sensor 10 can be guided on the guide faces 14a and smoothly mounted on the sensor mounting part 8 of the biological information measurement device 5.

Furthermore, the rectangular tubular protuberance 14 covers the entire outer circumference of the sensor insertion opening 13, which strengthens the circumference of the sensor insertion opening 13. Therefore, the sensor insertion opening 13 will not be torn by a blood glucose level sensor 10 during its insertion.

Still further, since the rectangular tubular protuberance 14 provided at the sensor insertion opening 13 strengthens the circumference of the sensor insertion opening 13, the sensor insertion opening 13 is prevented from being torn when the biological information measurement device 5 is inserted through the display viewable window 12.

Particularly, if the sensor insertion opening 13 provided at the elastic cover body 1 was only a hole, the sensor insertion opening 13 could be stretched out and torn by the insertion of the biological information measurement device 5. In this embodiment, however, the sensor insertion opening 13 has the tubular protuberance 14 and therefore, is prevented from being torn.

Should the cover body 1 become dirty, the user can clean the outer surface of the cover body 1 having the biological information measurement device 5 therein, using a washcloth or the like. The user may remove the cover body 1 from the biological information measurement device 5 and clean the removed cover body 1.

As discussed above, the protective cover for a biological information measurement device in this embodiment is provided with the protuberance 14 so as to correspond to the sensor mounting part 8 of the body case 6 of the biological information measurement device 5. Therefore, the finger of a user cannot easily reach the sensor mounting part 8 of the biological information measurement device 5, which reduces the risk of infection.

In this embodiment, the cover body 1 is integrally formed of the upper side 2, lower side 3 and lateral side 4 having silicon rubber as an example of an elastic member. The upper side 2 with the operating portions 15 shown in FIG. 1 is preferably formed thinner than the lower side 3 and the lateral side 4. In particular, the upper side 2 is preferably 1 mm thick, and the lower side 3 and the lateral side 4 are preferably each 2 mm thick. Having such a thin upper side 2, the operating buttons 9 are easy to operate.

Specifically, the entire upper side 2 of the cover body 1 is thinner than the lower side 3 and the lateral side 4. In this way, the operating portions 15 and their periphery area become transparent. Therefore, the user can see the operating buttons 9 of the biological information measurement device 5 corresponding to the operating portions 15. A user can also see indications printed on the operating buttons 9 and on the periphery of the operating buttons 9.

Furthermore, since the operating portions 15 are thin and soft, the user will likely not incorrectly press a neighboring button among the plurality of closely aligned operating buttons 9. As a result, the device is easy to operate while the risk of infection is reduced.

Should the user accidentally drop the biological information measurement device 5 covered by the cover body 1, the thick lower side 3 and lateral side 4, will effectively absorb the impact of the drop. This will thereby protecting the biological information measurement device 5.

The periphery of the display part 7 of the biological information measurement device 5 is protected by the preferably 1 mm thick upper side 2 of the cover body 1. Therefore, the display part 7 of the biological information measurement device 5 will not directly touch the surface onto which it has dropped and so the display part 7 will be protected by the cover body 1.

According to this embodiment, the upper side 2, lower side 3, and lateral side 4 are colored in white (or a color similar to white). Therefore, when using the biological information measurement device 5, should the blood of the user accidentally spatters and stains the cover body 1, the user can easily recognize the stain on the white cover body 1.

The lateral side 4, which is most easily stained with blood, is sufficiently thick around the sensor insertion opening 13. Therefore, the user cannot see the biological information measurement device 5 through the lateral side 4. This makes the white color of the lateral side 4 around the sensor insertion opening 13 brighter. As a result, the user can easily recognize the stain on the outer lateral side.

In this embodiment, the outer lateral side of the cover body 1 has only one opening, the sensor insertion opening 13. Therefore, the biological information measurement device 5 can be more resistant to static electricity.

Particularly, if static electricity is transmitted to the biological information measurement device 5 via the blood glucose level sensor 10 shown in FIG. 2, it will reach the inside of the biological information measurement device 5. It may be passed through joints between the upper case 6a, lower case 6b, and battery cover 6c of the biological information measurement device 5, and thereby damage the electronic components inside the device.

In this Embodiment, the biological information measurement device 5 is covered by the cover body 1 made of insulating material. Typically, static electricity is transmitted along the outer surface of the cover body 1 and then to the joints between the upper case 6a, lower case 6b, and battery cover 6c of the biological information measurement device 5. In this case, however, since the distance over which static electricity must be transmitted through the insulation surface is longer, the electronic components inside the biological information measurement device 5 will not be damaged by the transmission of static electricity.

As a result, the biological information measurement device 5 can be more resistant to static electricity.

As discussed above, the protective cover for a biological information measurement device according to this embodiment includes operating portions 15 on the upper side 2 of the cover body 1 between the display viewable window 12 and the sensor insertion opening 13. Furthermore, the operating portions 15 are formed thinner than the lower side 3 and the lateral side 4 so that the operating portions 15 are transparent. With this configuration, the user can see the operating buttons 9 of the biological information measurement device 5 corresponding to the operating portions 15 and so the user will not incorrectly press a neighboring button 9. As a result, the device is easy to operate while the risk of infection is reduced.

The following is a description of a protective cover for a biological information measurement device according to an embodiment of the present invention. Some of the same elements of the protective cover in this embodiment are denoted by the same reference symbols as those in a previously discussed embodiment, and detailed description of such elements will be omitted here.

Figure 5:
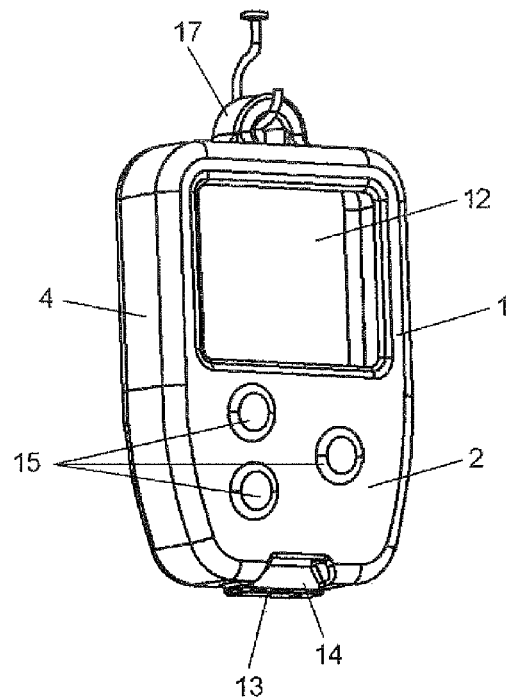
FIG. 5 is a perspective view of a protective cover for a biological information measurement device, according to an embodiment of the present invention.

The protective cover for a biological information measurement device is different from a previously discussed cover body 1 in that it includes a suspender ring 17 on one end of the lateral side 4 opposite the sensor insertion opening 13, as shown in FIG. 5. With this configuration, the user can rinse out the cover body 1 with cleaning liquid and hang it on a hook in a dryer, for example, using the suspender ring 17. This makes the device easy to use.

The lateral side 4 provided with the suspender ring 17 is formed thicker than the upper side 2 as discussed above, thereby providing a sufficient strength for hanging.

Furthermore, as shown in FIG. 5, when the cover body 1 is hung, cleaning liquid droplets remaining inside the cover body 1 fall via gravity along the inner face of the cover body 1, then move down to and through the sensor insertion opening 13, and finally out of the cover body 1. This also makes the device easy to use.

The following is a description of a protective cover for a biological information measurement device according to an embodiment of the present invention. Some of the same elements of the protective cover in this embodiment are denoted by the same reference symbols as those in previous embodiments, and detailed description of such elements will be omitted here.

Figure 6:
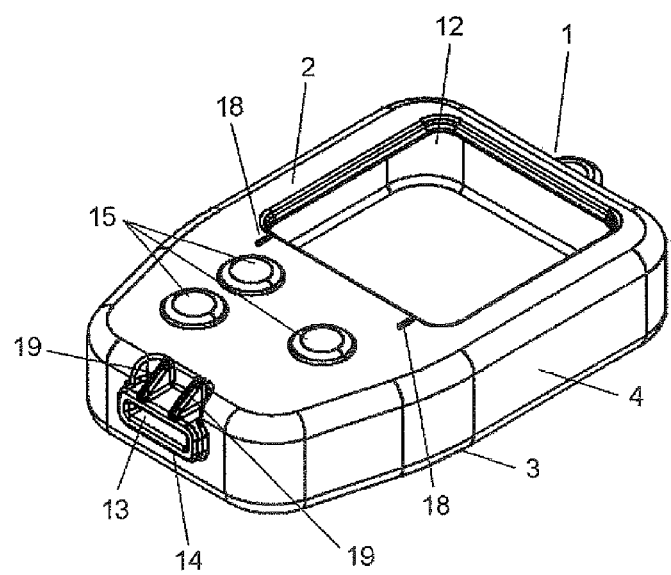
FIG. 6 is a perspective view of a protective cover for a biological information measurement device, according to an embodiment of the present invention.

The protective cover for a biological information measurement device may include display alignment marks 18 on the upper side of the cover body 1 for alignment with an outer periphery of the display part 7 of the biological information measurement device 5, as shown in FIG. 6. The display alignment marks 18 are projections extending from the display viewable window 12 toward the sensor insertion opening 13.

Since the cover body 1 is soft and elastic as discussed above, it can be slightly deformed to fit the periphery of the biological information measurement device 5 when inserted into the biological information measurement device 5. This may cause misalignment between the sensor insertion opening 13 of the cover body 1 and the sensor mounting part 8 of the biological information measurement device 5. Therefore, it is necessary to correctly align the cover body 1 with the biological information measurement device 5.

As shown in FIG. 6, the upper side 2 of the cover body 1 may be provided with the display alignment marks 18 for alignment with the lateral sides of the display part 7 of the biological information measurement device 5. In particular, when putting the cover body 1 on the biological information measurement device 5, the user can only align the lateral sides of the display part 7 of the biological information measurement device 5 with the display alignment marks 18 to correctly align the cover body 1 and the biological information measurement device 5. As a result, the sensor insertion opening 13 of the cover body 1 is aligned with the sensor mounting part 8 of the biological information measurement device 5. This enables a blood glucose level sensor 10 to be smoothly inserted into the sensor mounting part 8 through the sensor insertion opening 13.

As shown in FIG. 6, sensor alignment marks 19 are provided at the outer periphery of the sensor insertion opening 13 near the upper side 2 so as to align with the width of a blood glucose level sensor 10. Therefore, the user can insert a blood glucose level sensor 10 correctly into the sensor mounting part 8 (FIG. 2) by inserting it in alignment with the sensor alignment marks 19 even when the sensor mounting part 8 is difficult to see.

The sensor alignment marks 19 are projections extending from the front end of the sensor insertion opening 13 to the back side (toward the sensor mounting part 8). These projections strengthen the tubular protuberance 14.

The sensor alignment marks 19 are provided on the outer periphery of the sensor insertion opening 13 near the upper side 2. Alternatively, they may be provided on the inner periphery of the sensor insertion opening 13.

As discussed above, the protective cover for a biological information measurement device preferably covers the outer circumferential lateral side of the body case of the biological information measurement device as well as its upper and lower sides. In this way, blood is prevented from going into joints between the upper and lower sides of the body case. This reduces the risk of infection caused by the blood adhering to the body case.

Furthermore, the protective cover may include a protuberance at a portion corresponding to the sensor mounting part of the biological information measurement device. In this way, the sensor mounting part of the biological information measurement device cannot be easily touched by a user's finger. This also reduces the risk of infection.

Still further, the protective cover for a biological information measurement device according to the present invention on the upper side is formed thinner on the upper side than the lower and lateral sides so that the operating portions are transparent. In this way, the user can easily recognize the operating buttons of the biological information measurement device through the operating portions. As a result, the user is prevented from incorrectly pressing a neighboring button and can operate the device easily.

Embodiments of the present invention may serve as a protective cover for a biological information measurement device that measures biological information such as a blood glucose level in blood. They may also serve as a biological information measurement device covered by the protective cover.

The invention claimed is:

1. A protective cover for a biological information measurement device, comprising:
   an upper side;
   a lower side opposing the upper side with a predetermined area therebetween; and
   a lateral side extending along a side circumference of the protective cover between the upper side and the lower side,
   wherein the upper side, the lower side, and the lateral side are integrally formed of an elastic member,
   the upper side includes at a first end thereof a display viewable window,
   the lateral side includes a sensor insertion opening at a second end opposite the first end with the display viewable window on the upper side, and
   the sensor insertion opening includes a tubular protuberance configured to cover an outer circumference of the sensor insertion opening and protrude outwardly from the sensor insertion opening,
   wherein the tubular protuberance protrudes in a direction opposite an insertion direction of a sensor and towards the sensor insertion opening and is rectangular and has a front end opening larger than the sensor insertion opening.

2. The protective cover for a biological information measurement device according to claim 1, wherein the upper side, the lower side, and the lateral side are integrally formed of silicon rubber.

3. The protective cover for a biological information measurement device according to claim 1, wherein an operating portion bulges from the upper side.

4. The protective cover for a biological information measurement device according to claim 1, wherein the tubular protuberance and the lateral side are integrally formed.

5. The protective cover for a biological information measurement device according to claim 1, wherein the rectangular tubular protuberance has an inclined face extending from the front end opening toward the sensor insertion opening.

6. The protective cover for a biological information measurement device according to claim 1, wherein an outer circumference of the display viewable window includes a display alignment mark for alignment with a display part of the biological information measurement device.

7. The protective cover for a biological information measurement device according to claim 1, wherein the tubular protuberance includes a sensor alignment mark for alignment with a width of a sensor.

8. The protective cover for a biological information measurement device according to claim 1, wherein the upper side, the lower side, and the lateral side are white in color.

9. The protective cover for a biological information measurement device according to claim 1, wherein the lateral side includes a suspender ring at an end opposite the sensor insertion opening.

10. The protective cover according to claim 1, wherein the upper side includes an operating portion between the display viewable window and the sensor insertion opening, and the operating portion being thinner than the lower side and the lateral side.

11. A biological information measurement device with a protective cover wherein
    the biological information measurement device includes:
       a body case inserted in the protective cover body through the display viewable window;
       a display part provided at an upper side of the body case so as to correspond to the display viewable window;
       a sensor mounting part provided at a lateral side of the body case so as to correspond to the sensor insertion opening; and
       an operating button provided at the upper side of the body case;
    the protective cover includes:
       an upper side;
       a lower side opposing the upper side with a predetermined area therebetween; and
       a lateral side extending along a side circumference of the protective cover between the upper side and the lower side,
       wherein the upper side, the lower side, and the lateral side are integrally formed of an elastic member,
       the upper side includes at a first end thereof a display viewable window,
       the lateral side includes a sensor insertion opening at a second end opposite the first end with the display viewable window on the upper side, and
       the sensor insertion opening includes a tubular protuberance configured to cover an outer circumference of the sensor insertion opening and protrude outwardly from the sensor insertion opening.

12. The biological information measurement device according to claim 11, wherein the operating button bulges from the upper side of the body case.

13. The biological information measurement device according to claim 12, comprising a plurality of operating buttons.

* * * * *